(12) United States Patent
Gross et al.

(10) Patent No.: US 12,274,806 B2
(45) Date of Patent: Apr. 15, 2025

(54) METHODS AND SYSTEMS FOR INDICATING A SANITATION STATUS OF A SURFACE

(71) Applicant: The Boeing Company, Chicago, IL (US)

(72) Inventors: Gwen Marie Lanphere Gross, Redmond, WA (US); Xiaoxi Wang, Mukilteo, WA (US); Kjersta L. Larson-Smith, Seattle, WA (US)

(73) Assignee: THE BOEING COMPANY, Arlington, VA (US)

( * ) Notice: Subject to any disclaimer, the term of this patent is extended or adjusted under 35 U.S.C. 154(b) by 841 days.

(21) Appl. No.: 17/468,744

(22) Filed: Sep. 8, 2021

(65) Prior Publication Data

US 2022/0152258 A1    May 19, 2022

Related U.S. Application Data (60) Provisional application No. 63/115,642, filed on Nov. 19, 2020.

(51) Int. Cl.
*A61L 2/28* (2006.01)
(52) U.S. Cl.
CPC .............. *A61L 2/28* (2013.01); *A61L 2202/11* (2013.01); *A61L 2202/25* (2013.01)
(58) Field of Classification Search
CPC ................................. A61L 2/28; A61L 2202/11
See application file for complete search history.

(56) References Cited

U.S. PATENT DOCUMENTS

| | | | |
|---|---|---|---|
| 6,316,108 B1 | 11/2001 | Tabor et al. | |
| 8,242,162 B2 | 8/2012 | Meador et al. | |
| 8,999,718 B2 | 4/2015 | Catalano | |
| (Continued) | | | |

FOREIGN PATENT DOCUMENTS

| | | | | |
|---|---|---|---|---|
| EP | 3231447 | | 10/2017 | |
| WO | WO 01-45755 | * | 6/2001 | ........... G01N 31/226 |
| WO | WO01/86289 | | 11/2001 | |
| WO | WO-0186289 A1 | * | 11/2001 | ............... A61L 2/07 |

OTHER PUBLICATIONS

Schoene, et al. (Year: 2001).*
(Continued)

*Primary Examiner* — Jill A Warden
*Assistant Examiner* — Alex Ramirez
(74) *Attorney, Agent, or Firm* — MH2 Technology Law Group LLP (57) ABSTRACT

A method for indicating a sanitation status of a surface may comprise contacting a coating on a surface with a cleaning composition, wherein the coating comprises a chromic material and exhibits a baseline optical state under illumination with light having a first wavelength prior to contact with the cleaning composition and an altered optical state under illumination with light having a second wavelength after contact with the cleaning composition, the cleaning composition configured to induce a switch from the baseline optical state to the altered optical state; and illuminating the coating with the first wavelength of light, the second wavelength of light, or both, to reveal a sanitation status of the surface. Systems for indicating a sanitation status of a surface are also provided.

20 Claims, 5 Drawing Sheets

(56) References Cited

U.S. PATENT DOCUMENTS

| | | |
|---|---|---|
| 10,512,704 B2 | 12/2019 | Dytioco et al. |
| 2007/0231188 A1 | 10/2007 | June et al. |
| 2011/0315591 A1 | 12/2011 | Lespinasse et al. |
| 2015/0079690 A1 | 3/2015 | Burns et al. |
| 2018/0369440 A1* | 12/2018 | Dytioco ................. G01N 21/94 |
| 2020/0047868 A1 | 2/2020 | Young et al. |
| 2022/0096680 A1 | 3/2022 | Mcintosh |

OTHER PUBLICATIONS

Extended European Search Report for EP Appl. No. 23202264 dated Jan. 11, 2024.

Bryant et al. "A rapidly-reversible absorptive and emissive vapochromic Pt(II) pincer-based chemical sensor," Nature Communications, 8 Article No. 1800 (2017) 9 pages.

Ascherl et al., "Solvatochromic covalent organic frameworks," Nature Communications 9, Article No. 3802 (2018), 8 pages.

Choi et al "Solvatochromic fluorescence in an immiscible two-phase system of alcohols and hydrophobic polymyers: Distinction between light alcohol and water, ink printing," Polymer 141 (2018) 194-201.

Dong et al., "Solvatochromism based on structural color. Smart polymer composites for sensing and security," Materials and Design 160 (2018) 417-426.

Wang et al. "Vapochromic behavior of MOF for selective sensing of ethanol," Spectrochimica Acta Part A: Molecular and Biomolecular Spectroscopy, 194 (2018) 158-162.

Extended Search Report for EP21200282.8, mailed Mar. 23, 2022.

* cited by examiner

METHODS AND SYSTEMS FOR INDICATING A SANITATION STATUS OF A SURFACE

CROSS-REFERENCE TO RELATED APPLICATIONS

The present application claims priority to U.S. provisional patent application No. 63/115,642 that was filed Nov. 19, 2020, the entire contents of which are incorporated herein by reference.

BACKGROUND

Diseases with epidemic potentials represent a major global challenge. Some diseases are readily transmitted between people by pathogen-laden droplets impinging on high-touch surfaces. High-touch surfaces are ubiquitous in vehicles such as automobiles and aircraft. There are many effective disinfection strategies available for such surfaces, including frequent application of chemical cleaning products and disinfectants. However, despite use of such disinfection strategies, users of these vehicles may not be aware whether the high-touch surfaces have been cleaned or not, leading to concerns about potential disease transmission.

SUMMARY

Provided are methods and systems for indicating a sanitation status of a surface.

Methods for indicating a sanitation status of a surface are provided. In an embodiment 1, such a method comprises contacting a coating on a surface with a cleaning composition, wherein the coating comprises a chromic material and exhibits a baseline optical state under illumination with light having a first wavelength prior to contact with the cleaning composition and an altered optical state under illumination with light having a second wavelength after contact with the cleaning composition, the cleaning composition configured to induce a switch from the baseline optical state to the altered optical state; and illuminating the coating with the first wavelength of light, the second wavelength of light, or both, to reveal a sanitation status of the surface.

An embodiment 2 is the method according to embodiment 1, wherein the first wavelength of light is provided by ambient light and the second wavelength of light is provided by ambient light, ultraviolet (UV) light, or infrared (IR) light.

An embodiment 3 is the method according to embodiment 2, wherein the UV light is UVA light.

An embodiment 4 is the method according to any of the preceding embodiments, further comprising applying a coating composition comprising the chromic material to the surface to form the coating thereon.

An embodiment 5 is the method according to any of the preceding embodiments, wherein the baseline optical state is clear under illumination with ambient light and the altered optical state is colored under illumination with ambient light.

An embodiment 6 is the method according to any of the preceding embodiments, wherein the baseline optical state is clear under illumination with ambient light and the altered optical state is photoemissive under illumination with UV light or IR light.

An embodiment 7 is the method according to any of the preceding embodiments, wherein the baseline optical state is colored under illumination with ambient light and the altered optical state is colored under illumination with ambient light.

An embodiment 8 is the method according to any of the preceding embodiments, wherein the baseline optical state is colored under illumination with ambient light and the altered optical state is photoemissive under illumination with UV light.

An embodiment 9 is the method according to any of the preceding embodiments, wherein the switch from the baseline optical state to the altered optical state is reversible.

An embodiment 10 is the method according to any of the preceding embodiments, wherein the altered optical state is maintained for at least 30 minutes.

An embodiment 11 is the method according to any of the preceding embodiments, wherein the coating is formed from a coating composition comprising the chromic material and a polymeric base formulation.

An embodiment 12 is the method according to embodiment 11, wherein the polymeric base formulation is a parylene base formulation, an epoxy base formulation, a polyurethane base formulation, or a polyester base formulation.

An embodiment 13 is the method according to any of the preceding embodiments, wherein the coating is in the form of a pre-defined image.

An embodiment 14 is the method according to any of the preceding embodiments, wherein the surface is part of an internal cabin of a vehicle.

An embodiment 15 is the method according to embodiment 14, wherein the vehicle is a non-aerospace vehicle.

An embodiment 16 is method according to embodiment 14, wherein the vehicle is an aerospace vehicle.

An embodiment 17 is the method according to embodiment 1, wherein the cleaning composition is configured to eliminate a pathogen on the surface.

Systems for indicating a sanitation status of a surface are also provided. In an embodiment 18, such a system comprises a coating on a surface of an internal cabin of a vehicle, wherein the coating comprises a chromic material and exhibits a baseline optical state under illumination with light having a first wavelength prior to contact with a cleaning composition and an altered optical state under illumination with light having a second wavelength after contact with the cleaning composition, the cleaning composition is configured to induce a switch from the baseline optical state to the altered optical state.

An embodiment 19 is the system according to embodiment 18, further comprising one or more light sources configured to illuminate the coating with light having the first wavelength, light having the second wavelength, or both.

An embodiment 20 is the system according to any of embodiments 18-19, further comprising the cleaning composition.

Vehicles are also provided which comprise an internal cabin having a surface, the vehicle further comprising the system according to any of embodiments 18-20.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

In one aspect, methods for indicating a sanitation status of a surface are provided. In embodiments, such a method comprises contacting a coating on a surface with a cleaning composition, wherein the coating comprises a chromic material and exhibits a baseline optical state under illumination with light having a first wavelength prior to contact with the cleaning composition and an altered optical state under illumination with light having a second wavelength after contact with the cleaning composition. The cleaning composition is configured to induce a switch from the baseline optical state to the altered optical state. As further described below, the baseline optical state of the coating and the altered optical state of the coating are different, while the first and second wavelengths of light may be the same or may be different. As also described below, the baseline optical state is indicative of a sanitation status (e.g., has not been cleaned) of the surface while the altered optical state is indicative of another, different sanitation status (e.g., has been cleaned) of the surface. The method may comprise illuminating the coating with the first wavelength of light, the second wavelength of light, or both. Illumination reveals the baseline and altered optical states of the coating, thereby communicating to a viewer the sanitation status of the surface. The method may comprise applying a coating composition comprising the chromic material to the surface to form the coating thereon.

The phrase "optical state" refers to a state of appearance of the coating under illumination with light having a wavelength. This wavelength may refer to a single wavelength of the light or a range of wavelengths of the light. The light may be "ambient" light comprising a range of wavelengths. This includes ambient sunlight and ambient room light. For example, ambient sunlight comprises visible light having wavelengths of between about 400 and about 700 nm, ultraviolet (UV) light having wavelengths of less than about 400 nm (e.g., about 100 nm to about 400 nm), and infrared (IR) light having wavelengths of greater than about 800 nm (e.g., about 800 nm to about 1 mm). Regarding UV light, the UV light may be UVA light having wavelengths of about 315 nm to about 400 nm. The wavelengths of ambient room light depend upon the source of the light (e.g., various types of light bulbs), but ambient room light may encompass similar wavelength ranges. Other light sources may be used for the illumination, e.g., a UV light wand having a single UV wavelength (e.g., 254 nm) or a range of UV wavelengths (e.g., 315 to 400 nm).

An optical state may be "clear," a state that refers to transmitting visible light. The transmission need not be 100% of the visible light through the coating, e.g., transmission may be at least 95%, at least 98%, or a least 99%. An optical state may be "colored," a state that refers to transmitting a particular wavelength range within visible light (while absorbing others) or reflecting a particular wavelength range within visible light. Red, orange, yellow, green, blue, purple, etc. are illustrative colored optical states. The percent transmission/reflection at these wavelength ranges need not be a specific value, but will generally that which results in a color detectable by the naked eye. The term "colored" also refers to white (reflecting substantially all wavelengths of visible light) and black (absorbing substantially all wavelengths of visible light). An optical state may be "photoemissive," a state that refers to the emission of light induced by the absorption of photons. For example, fluorescent and phosphorescent are illustrative photoemissive states. The wavelength of the emitted light from a photoemissive coating may also distinguish photoemissive states, e.g., fluorescent red and fluorescent orange represent different optical states. The emission need not have a specific intensity, but will generally be sufficient to be detectable by the naked eye.

In embodiments, the baseline optical state is clear under illumination with ambient light and the altered optical state is colored under illumination with ambient light. In embodiments, the baseline optical state is clear under illumination with ambient light and the altered optical state is photoemissive (e.g., fluorescent) under illumination with UV light. In embodiments, the baseline optical state is colored under illumination with ambient light and the altered optical state is colored (a different colored optical state) under illumination with ambient light. In embodiments, the baseline optical state is colored under illumination with ambient light and the altered optical state is photoemissive (e.g., fluorescent) under illumination with UV light. Other combinations may be used.

As noted above, the baseline optical state is indicative of a sanitation status of the surface on which the coating is formed, while the altered optical state is indicative of another, different sanitation status. The switch from baseline optical state to altered optical state is induced by contacting the coating/surface with the cleaning composition. Thus, the sanitation status may be switched from "not clean" (prior to contact) to "clean" (after contact). However, the term "not clean" does not necessarily mean that the coating/surface is contaminated, just that it has not been exposed to the cleaning composition within the lifetime of the altered optical state of the coating.

The chromic material of the coating/coating composition is the component which is primarily responsible for the optical behavior of the coating. However, other components of the coating/coating composition may influence the coating's optical state under illumination. A variety of chromic materials may be used. Chromic materials exhibit environment-dependent optical responses spanning the optical states described above, although the mechanism by which the optical response/state is induced may differ. For example, the optical response may be due to a perturbance of crystal structure, electronic structure, or refractive index, e.g., due to the presence of certain components of the cleaning composition in contact with the chromic material. Suitable chromic materials include vapochromic materials (exhibiting an optical response in the presence of certain vapors) and solvatochromic materials (exhibiting an optical response in the presence of certain solvents).

By way of illustration, platinum (Pt)(II)-pincer complexes are organometallic compounds which may be used as the chromic material. Illustrative Pt(II)-pincer complexes include $Pt(Me_2bzimpy)Cl]PF_6$ ($Me_2bzimpy$=2,6-bis(N-methylbenzimidazol-2-yl)pyridine); $Pt(Me_2bzimpy)Cl]Cl$; $Pt(Nttpy)Cl]$ (Nttpy=4'-(p-nicotinamide-N-methylphenyl)2,2':6',2"-terpyridine); and combinations thereof. Certain metal-organic framework materials may be used as the chromic material, such as $Co_3[Co(CN)_6]_2$ nanoparticles. Certain core-shell nanoparticles capable of forming photonic crystal films may be used. For example, certain core-shell nanoparticles comprising a poly(methyl methacrylate)

(PMMA) core and a poly(ethyl acrylate)-co-poly(benzyl methacrylate) (PEA-co-PBzMA) shell can form transparent (clear) photonic crystal films. The transparency is due to use of a core-shell composition that provides a refractive index contrast (Δn) of about zero when the core-shell nanoparticles are assembled to form the photonic crystal (further described below). Solvatochromic dyes may also be used as the chromic material, either by themselves or in a functionalized form, e.g., covalently bound to a polymer or a polymerizable monomer. Each of these chromic materials exhibit environment-dependent optical responses spanning the optical states described above.

Selection of the chromic material for use in the present methods depends upon the desired optical states for the coating, e.g., a clear or colored baseline optical state and a colored or photoemissive altered optical state. The chromic material is also desirably one that exhibits a reversible optical response such that the coating can be switched between the baseline optical state and the altered optical state multiple times over a period of time. In embodiments, the number of times is at least 50 per month, at least 100 per month, or at least 150 per month. In embodiments, the number of times is at least 100 over 3 months, at least 365 times over a year, or at least 2000 times over 5 years. Selection of the chromic material may also be guided by a desired timescale for the optical responses. For example, it is desirable that the chromic material is one that enables the coating to achieve the altered optical state relatively quickly. In embodiments, this means achieving the altered optical state within a few seconds, including in from 1 second to 10 minutes, from 1 second to 1 minute, or from 1 second to 30 seconds. It is desirable that the chromic material is one that enables the altered optical state to be maintained for a relatively long period of time. In embodiments, this means maintaining the altered optical state for at least 30 minutes before switching back to the baseline optical state. This includes embodiments of at least 45 minutes, at least 60 minutes, at least 2 hours, or in a range of from 15 minutes to 5 hours.

Otherwise, selection of the chromic material for use in the present methods depends upon the desired surface to be coated as well as the cleaning composition to be used. The chromic material is desirably inert with respect to the surface to be coated, including surfaces which may be pre-coated with other materials. As further described below, as the cleaning composition provides the environment (e.g., pH, ionic molecules, solvent molecules, etc.) which induces the optical responses described above, the desired cleaning composition influences the selection of the chromic material. The application for which the present methods are to be carried out further guides selection of the chromic material. For example, in aerospace applications, the chromic material is desirably flame and smoke resistant.

In embodiments, the chromic material is itself capable of forming thin films such that other components need not be included in the coating composition from which the coating is formed. By way of illustration, the PMMA-PEA-co-PBzMA core-shell nanoparticles described above may be deposited onto a surface. Heat and pressure may be applied to facilitate assembly of the nanoparticles into thin films of a photonic crystal, thereby forming the coating.

In other embodiments, the coating composition may comprise a polymeric base formulation that provides additional components capable of forming thin polymeric films. The chromic material may be in the form of a solid or liquid dispersed throughout the resulting polymeric matrix. These additional components may include prepolymers and polymers. One or more of catalysts, hardeners, initiators, etc. may be included to induce polymerization and/or crosslinking reactions between prepolymers/polymers (i.e., to induce curing) in forming the coating from the coating composition. If curing is used, it is desirable that the polymeric base formulation is one that may be cured under relatively mild conditions, e.g., for thermal curing, using temperatures of 150° C. or less, 100° C., 50° C. or less, or room temperature.

A variety of polymeric base formulations may be used, including those used for forming parylene coatings, epoxy coatings, polyurethane coatings, and polyester coatings. For example, an illustrative parylene polymeric base formulation may comprise chloro-p-xylylene cyclic dimers; an illustrative epoxy polymeric base formulation may comprise bisphenol A diglycidyl ether monomers and either a polyaminoamide or a phenylenebis(methylamine); an illustrative polyurethane polymeric base formulation may comprise polymethylene polyphenyl polyisocyanate and either an aliphatic di-epoxy or an aliphatic di-amine; a polyester polymeric base formulation may comprise a phenolic functionalized polyester and a crosslinker as described in U.S. Pat. Pub. No. 20110315591 which is hereby incorporated by reference in its entirety; and a latex polymeric based formulation may comprise a polyurethane latex as described in U.S. Pat. No. 6,316,108 which is hereby incorporated by reference in its entirety. Other polymeric base formulations may be used.

In embodiments in which a polymeric base formulation is used, the amount of the chromic material in the coating composition may be selected to achieve a desired intensity of color/photoemission at the baseline and/or altered optical states of the coating. However, the amount is generally sufficiently low so as to avoid issues of contamination of the underlying surface with the chromic material. In embodiments, the amount of chromic material is in a range of from 1 weight % to 10 weight % (Here, weight % is (the total weight of the chromic material)/(total weight of the coating composition*100)). This includes a range of from 2 weight % to 8 weight % and from 1 weight % to 5 weight %. The balance may be the polymeric base formulation and if present, any additives.

Additives may be included in any of the coating compositions, e.g., surfactants and viscosity modifiers (e.g., Cab-o-sil® brand). Additives may be used in various suitable amounts, e.g., in a range of from 0.1 to 5 weight %, from 1 to 5 weight %, or from 0.1 to 2 weight %. (Here, weight % is (the total weight of the additives)/(total weight of the coating composition*100)). If not already provided by a polymeric base formulation, a liquid medium may be included in the coating composition, such as water, an organic solvent (e.g., methyl ethyl ketone, methyl isobutyl ketone, butyl acetate, acetylacetone, cyclohexanone, and mixtures thereof), etc.

A variety of techniques may be used to apply the coating composition to the surface. Such techniques include brushing, rolling, stamping, painting, spraying, etc. Other techniques include thin film deposition techniques such as dip coating, spin coating, etc. If curing is used as part of forming the coating, the present methods may further comprise apply the conditions necessary to induce curing.

The coatings formed by the present methods may be characterized by a thickness. Various thicknesses may be used, but generally, the coatings are relatively thin, e.g., less than 2 mm, less than 1 mm, less than 500 μm, less than 100 μm, or in a range of from 1 μm to 2 mm.

The coating formed from the coating composition may be shaped or patterned so as to form a pre-defined image (a graphic, text, grid pattern, etc.) visible to a viewer when the baseline optical state or altered optical state is colored or photoemissive. This may involve applying the coating composition in a pre-defined shape or pattern corresponding to the image, e.g., via a stamp, a printer, a mask, or a template. In other embodiments, the shaping/patterning may be achieved by forming coatings in which only selective regions of the coating are switched to the altered optical state upon contact with the cleaning composition. By way of illustration, this may be achieved by adding a photolabile crosslinker to the PMMA-PEA-co-PBzMA core-shell nanoparticles described above. Crosslinking between nanoparticles in the photonic crystal coating may be induced by directing the appropriate radiation through a photomask comprising the desired shape/pattern. The resulting photonic crystal coating will be crosslinked in only those regions illuminated by the radiation, i.e., crosslinked in the desired shape/pattern. This can result in only the uncrosslinked regions being switched to the altered optical state upon exposure to the cleaning composition and not the crosslinked regions, thereby revealing the image.

Surfaces on which the coating composition may be applied to form the coating are not particularly limited. By way of illustration, the surface may be a metal surface, a polymeric surface, a glass surface, or a composite thereof. The surfaces may include surfaces within a vehicle, e.g. an aerospace vehicle, an automotive vehicle, or other transportation vehicle. The phrase "aerospace vehicle" may refer to any device, craft, machine, used in the aerospace industry such as an aircraft such as an airplane; a rotorcraft; a marine vehicle such as a submarine; a space vehicle such as a space ship; a trajectory device; drone; satellite; fuselage; wing; composite; and the like. The phrase "automotive vehicle" may refer to any device, craft, machine, used in the automotive industry such as automobiles, buses, locomotives, train cars, and the like. The surface of the aerospace or automotive vehicle may be a high-touch surface such as portions of a seat (arms, sides, back, etc.), windows, trays, doors, knobs, handles, floors, keyboards, display screens, including surfaces in lavatories such as the sink handles, toilet flush button or handle, toilet seat, soap dispenser, paper holders, and other like lavatory surfaces, etc. By "high-touch surface" it is meant surfaces which experience frequent touching by users of the vehicles.

Various cleaning compositions may be used in the present methods. The cleaning composition, which is often a liquid, includes components that reduce or eliminate (e.g., at least 95%, at least 98%, at least 99%) various pathogens such as bacteria, viruses, fungi, mold, mildew, etc. when used as intended. As noted above, as the cleaning composition provides the environment that induces the optical response of the chromic material, the cleaning composition is also one that is sensitive to the selected chromic material. That is, the cleaning composition is "configured to" induce these optical responses by including those components to which the selected chromic material is optically responsive. The step of contacting the coating with the cleaning composition may involve application of the cleaning composition per its intended use, e.g., pouring, spraying, wiping, etc.

Cleaning compositions comprising alcohols such as ethanol, methanol, and ethoxylated alcohol may be used, as the optical properties of many chromic materials may be altered by such molecules. By way of illustration, as noted above, certain PMNIA-PEA-co-PBzMA core-shell nanoparticles assembled into a photonic crystal coating are transparent (clear) due a refractive index contrast ($\Delta n$) of about zero between the material of the core and the material surrounding the cores (the shells). Contacting the photonic crystal coating to a cleaning composition comprising ethanol can change the refractive index of the medium surrounding the cores, thereby resulting in a non-zero refractive index contrast. This refractive index contrast may be observed as a particular color (depending upon the size of the nanoparticles) upon illumination with visible light. This switch to the colored, altered optical state is reversible. As ethanol from the cleaning composition evaporates, the photonic crystal coating reverts back to its clear baseline optical state. As noted above, nanoparticles may be crosslinked in certain regions of the photonic crystal coating to suppress the switch to the colored, altered optical state within those regions.

Other cleaning compositions that may be used including aqueous cleaning compositions for chromic materials sensitive to water and peroxide cleaning compositions for chromic materials sensitive to acids (acid species may be generated by the peroxide components). Citrus-based cleaning compositions such as those comprising d-limonene may also be used for acid-sensitive chromic materials, as acid species may also be generated by the citrus-based components.

Figure 1A:
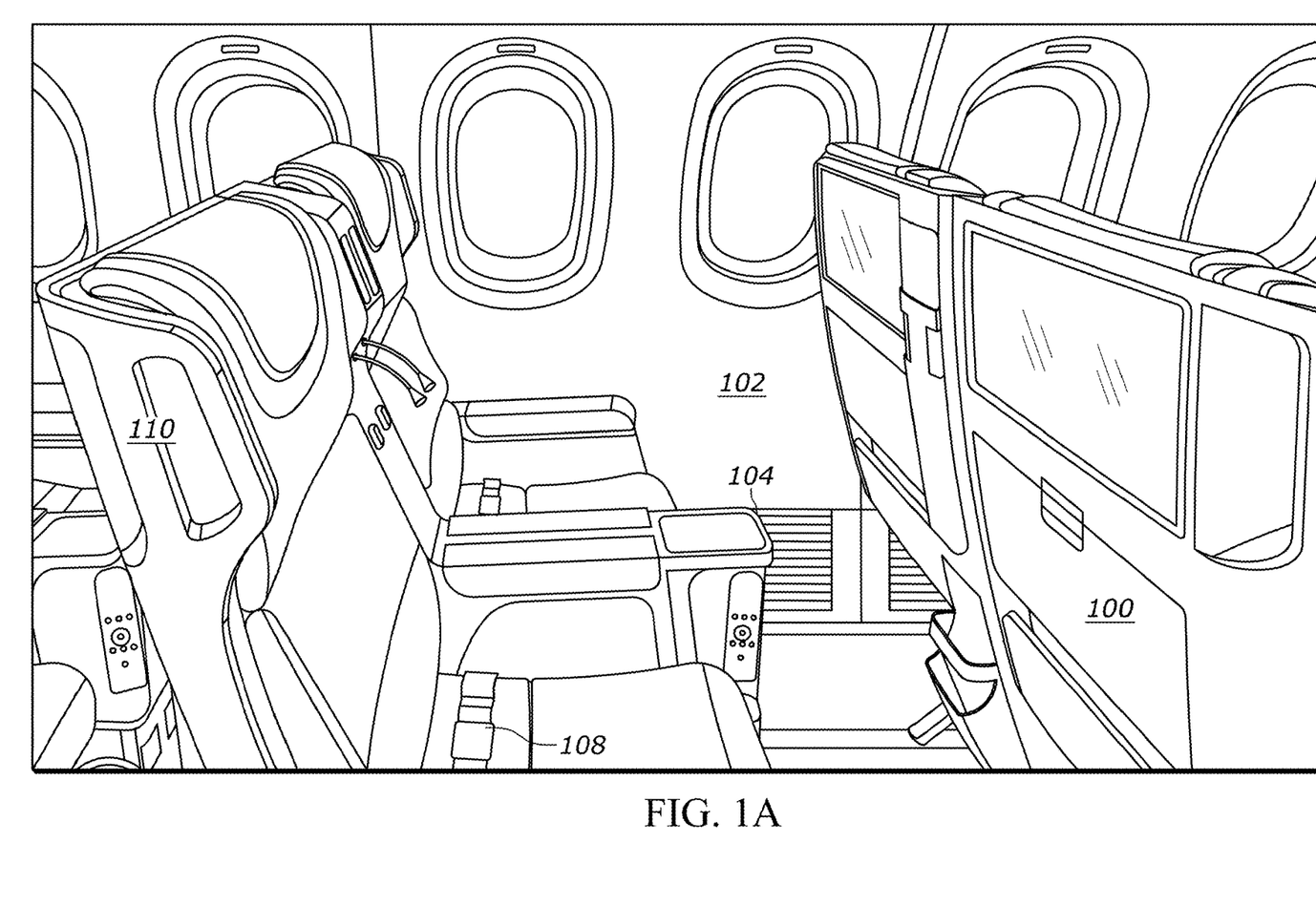
FIGS. 1A-1D illustrate steps of a method for indicating a sanitation status of a surface according to an illustrative embodiment.
Figure 1B:
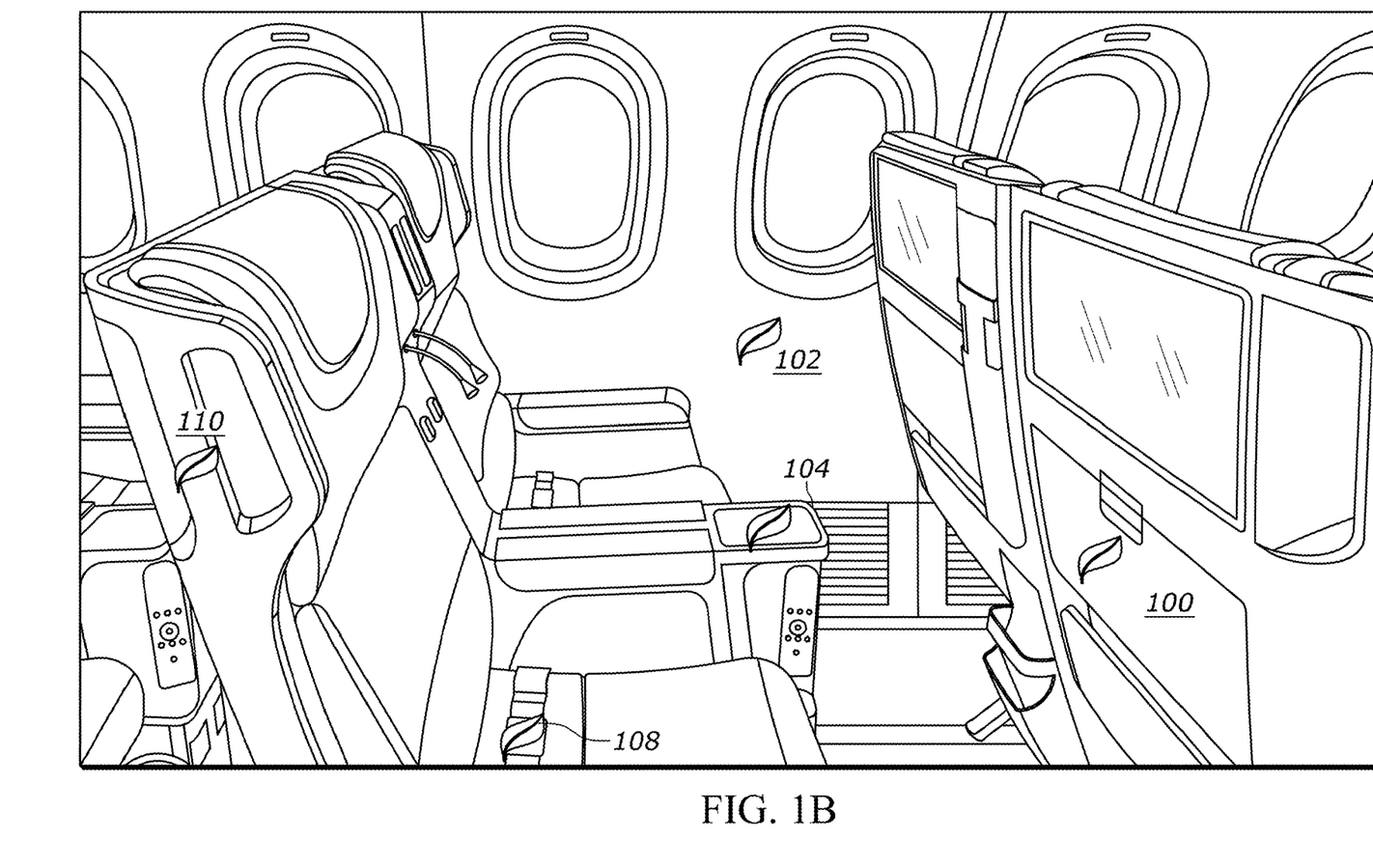
Figure 1C:
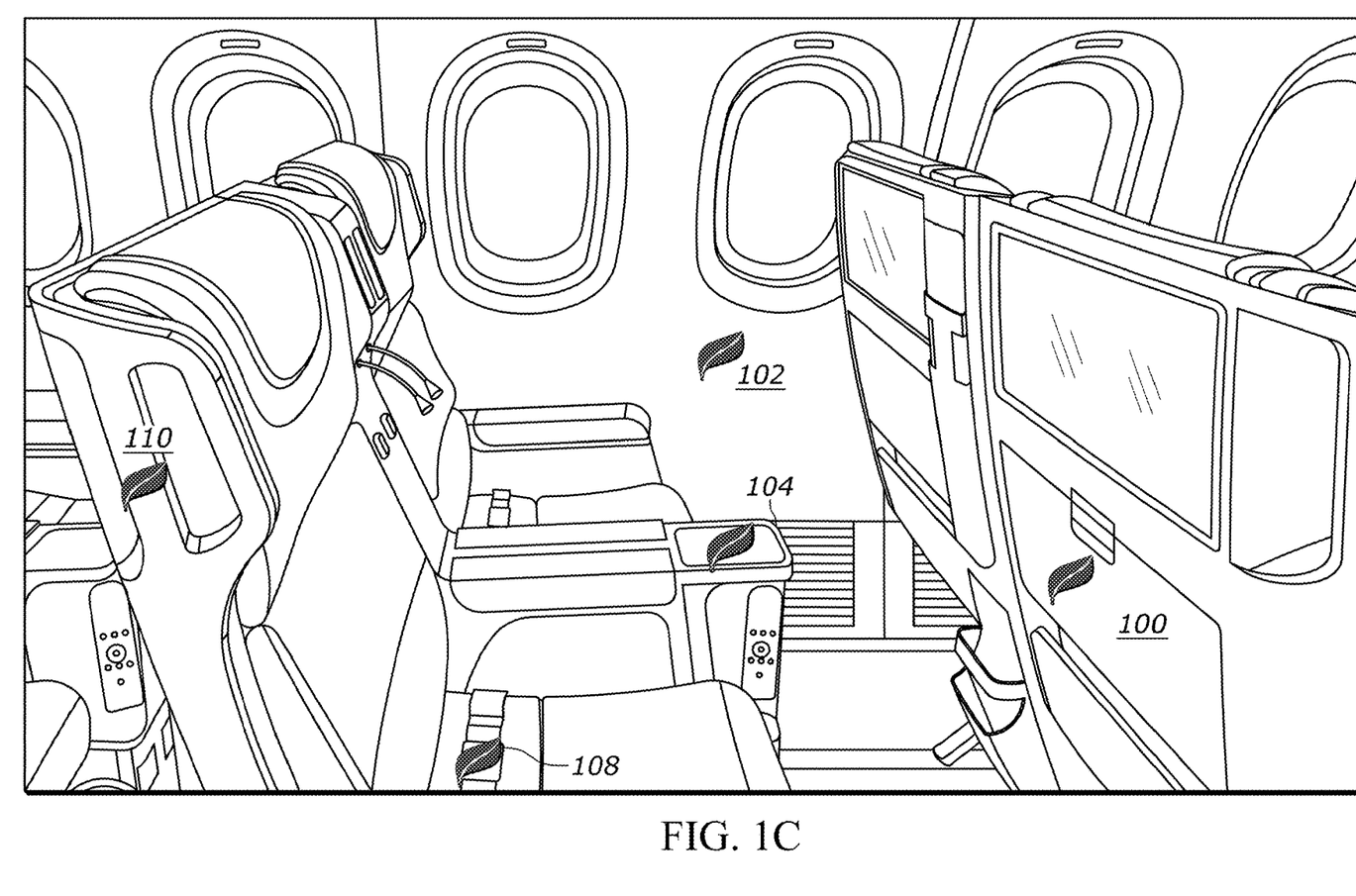
Figure 1D:
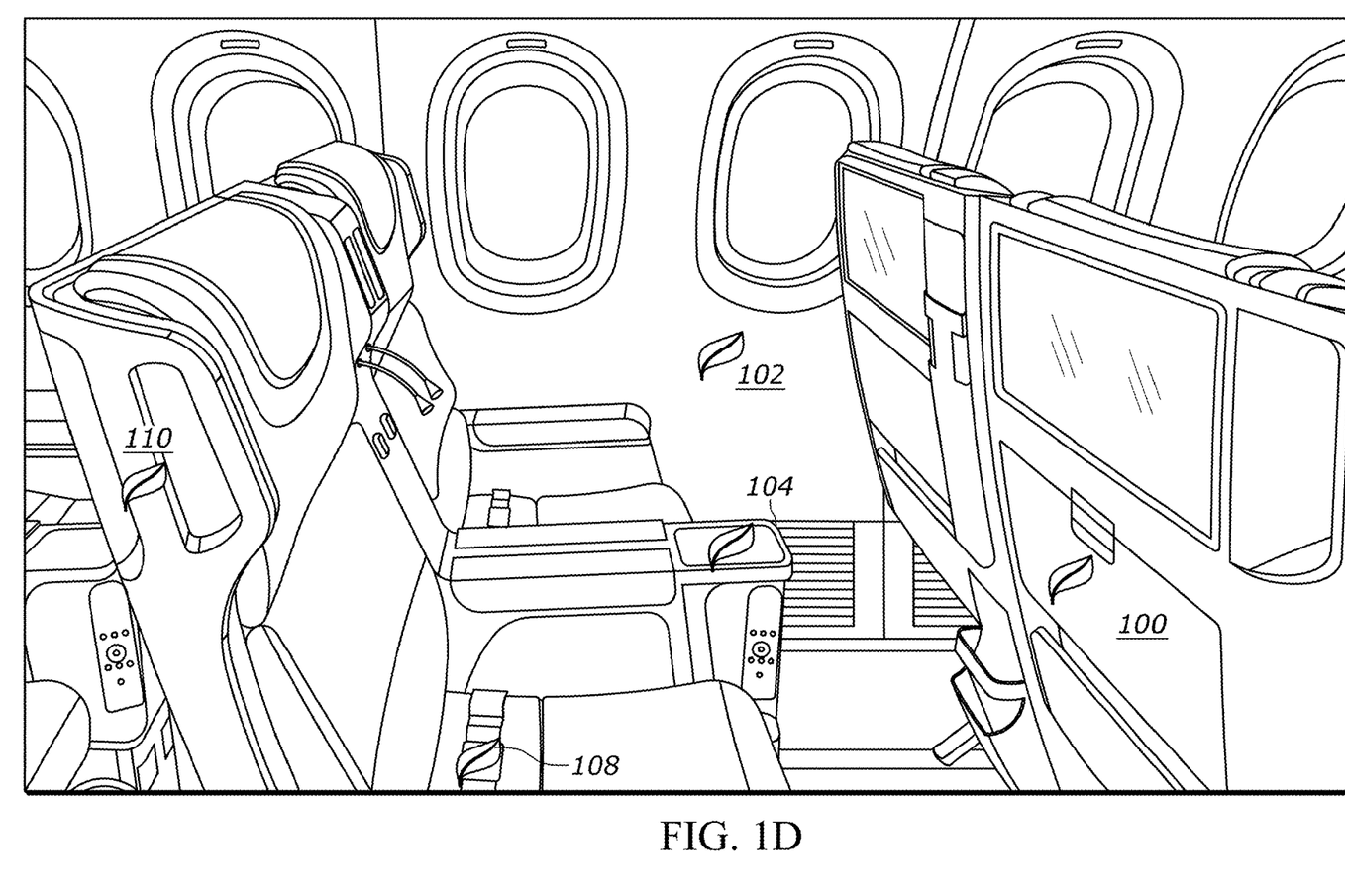

FIGS. 1A-1D are included to further illustrate the present disclosure. FIG. 1A shows a portion of an internal cabin of an airplane. Certain high-touch surfaces within internal cabin are labeled, a seat back 100 (or tray table), a wall 102, an arm tray 104, a seatbelt buckle 108, and a seat side 110. FIG. 1B shows the high-touch surfaces after application of a coating composition comprising a chromic material to the surfaces to form coatings thereon. In this embodiment, the coatings are in the shape of a graphic (leaf). Additional steps may have been conducted to form the coatings, such as curing. Under illumination with light (e.g., ambient light in the airplane), the coatings exhibit a clear baseline optical state. For convenience, the coatings are indicated with outlining, as their transparent nature may make them effectively invisible to a viewer. The transparent appearance indicates to a viewer that the surfaces have not been cleaned (or have not been cleaned in some period of time). FIG. 1C shows the surfaces after contacting the coating with a cleaning composition configured to induce a switch from the clear baseline optical state of the coating to an altered optical state of the coating. Under illumination with light (e.g., ambient light in the airplane or a UV light wand), the coatings exhibit a colored or photoemissive altered optical state. For convenience, the coatings are indicated with shading to represent the color/photoemission. The appearance of the altered optical state communicates to the viewer that the surfaces have been cleaned. FIG. 1D shows the surfaces after an extended period of time, e.g., 2 hours. The coatings have reverted back to their baseline optical states.

In another aspect, systems are provided which are configured to indicate a sanitation status of a surface. The systems may be used to carry out any of the present methods. In embodiments, such a system comprises a coating on a surface, the coating comprising a chromic material, wherein the coating exhibits a baseline optical state under illumination with light having a first wavelength prior to contact with a cleaning composition and the coating exhibits an altered optical state under illumination with light having a second wavelength after contact with the cleaning composition. Any of the coatings formed from the coating compositions described herein may be used. Any of the surfaces described herein may be used. The system may further comprise one or more light sources configured to provide the light having the first wavelength, light having the second wavelength, or both. For example, the light source may be one or more of a variety of types of light bulbs for providing room ambient light. The light source may be a UV light wand. The system may further comprise any of the cleaning compositions described herein.

Figure 2:
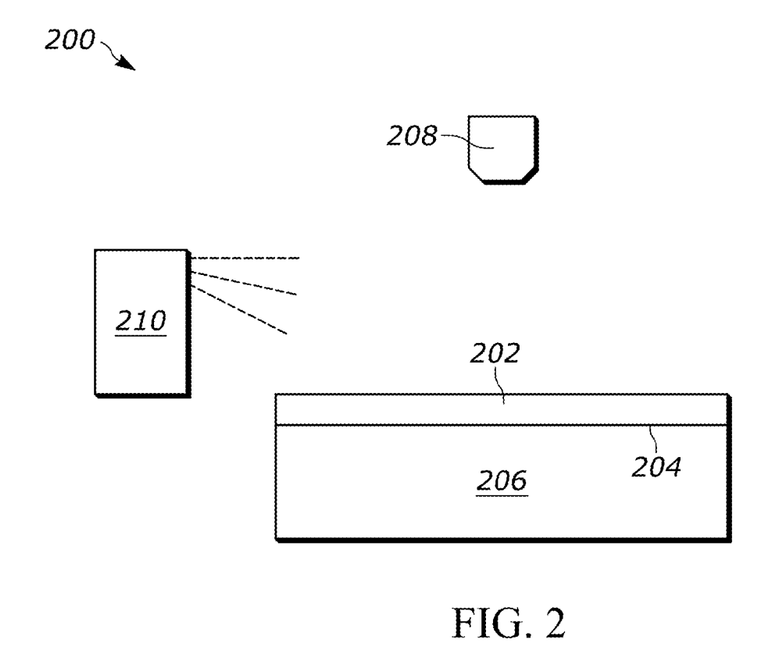
FIG. 2 is a schematic of a system configured to indicate a sanitation status of a surface according to an illustrative embodiment.

A schematic of an illustrative system 200 is shown in FIG. 2, comprising a coating 202 on a surface 204 of a component 206 of a vehicle (e.g., an airplane); a light source 208; and a cleaning composition 210. Vehicles comprising any of the disclosed systems are also encompassed by the present disclosure.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method for indicating a sanitation status of a surface, the method comprising:
    contacting a coating on a surface with a cleaning composition, wherein the coating comprises a chromic material and exhibits a baseline optical state under illumination with light having a first wavelength prior to contact with the cleaning composition and an altered optical state under illumination with light having a second wavelength after contact with the cleaning composition, the cleaning composition configured to induce a switch from the baseline optical state to the altered optical state; and
    illuminating the coating with the first wavelength of light, the second wavelength of light, or both, to reveal a sanitation status of the surface; and
    wherein the baseline optical state is clear under illumination with ambient light and the altered optical state is photoemissive under illumination with UV light or IR light.

2. The method of claim 1, wherein the first wavelength of light is provided by ambient light and the second wavelength of light is provided by, ultraviolet (UV) light, or infrared (IR) light.

3. The method of claim 2, wherein the second wavelength is UV light and the UV light is UVA light.

4. The method of claim 1, further comprising applying a coating composition comprising the chromic material to the surface to form the coating thereon.

5. The method of claim 1, wherein the baseline optical state is colored under illumination with ambient light and the altered optical state is photoemissive under illumination with UV light.

6. The method of claim 1, wherein the switch from the baseline optical state to the altered optical state is reversible.

7. The method of claim 1, wherein the altered optical state is maintained for at least 30 minutes.

8. The method of claim 1, wherein the coating is formed from a coating composition comprising the chromic material and a polymeric base formulation.

9. The method of claim 8, wherein the polymeric base formulation is a parylene base formulation, an epoxy base formulation, a polyurethane base formulation, or a polyester base formulation.

10. The method of claim 1, wherein the coating is in the form of a pre-defined image.

11. The method of claim 1, wherein the surface is part of an internal cabin of a vehicle.

12. The method of claim 11, wherein the vehicle is a non-aerospace vehicle.

13. The method of claim 11, wherein the vehicle is an aerospace vehicle.

14. The method of claim 1, wherein the cleaning composition is configured to eliminate a pathogen on the surface.

15. A system for indicating a sanitation status of a surface, the system comprising:
    a coating on a surface of an internal cabin of a vehicle, wherein the coating comprises a chromic material and exhibits a baseline optical state under illumination with light having a first wavelength prior to contact with a cleaning composition and an altered optical state under illumination with light having a second wavelength after contact with the cleaning composition, the cleaning composition is configured to induce a switch from the baseline optical state to the altered optical state; and
    wherein the baseline optical state of the coating is clear under illumination with ambient light and the altered optical state is photoemissive under illumination with UV light or IR light.

16. The system of claim 15, further comprising one or more light sources configured to illuminate the coating with light having the first wavelength, light having the second wavelength, or both.

17. The system of claim 15, further comprising the cleaning composition.

18. A vehicle comprising an internal cabin having a surface, the vehicle further comprising the system of claim 15.

19. The system of claim 15, wherein the coating is in the form of a pre-defined image.

20. The system of claim 15, wherein the cleaning composition is configured to eliminate a pathogen on a surface.

* * * * *